United States Patent

Anders et al.

[11] Patent Number: 6,017,482
[45] Date of Patent: *Jan. 25, 2000

[54] PROCESS FOR PRODUCING A FLEXIBLE PLASTIC GEL MOLDING WITH A PLURALITY OF CATHETERS EMBEDDED EQUIDISTANTLY THEREIN

[75] Inventors: Christine Anders; Reinhold Brathun, both of Haltern, Germany

[73] Assignee: Huels Aktiengesellschaft, Marl, Germany

[ * ] Notice: This patent issued on a continued prosecution application filed under 37 CFR 1.53(d), and is subject to the twenty year patent term provisions of 35 U.S.C. 154(a)(2).
This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/679,335

[22] Filed: Jul. 11, 1996

[30] Foreign Application Priority Data

Jul. 21, 1995 [DE] Germany .......................... 195 26 690

[51] Int. Cl.[7] .......................... B29C 39/10; A61M 36/04
[52] U.S. Cl. .......................... 264/257; 264/277; 604/283
[58] Field of Search .................................. 264/277, 257; 428/35.7, 36.9; 604/280, 283; 138/112; 600/3, 1, 6, 7, 8

[56] References Cited

U.S. PATENT DOCUMENTS

| 1,520,840 | 2/1924 | Murray | 138/111 |
|---|---|---|---|
| 3,554,379 | 1/1971 | Pye | 264/277 |
| 3,579,810 | 5/1971 | Mon | 264/277 |
| 3,708,071 | 1/1973 | Crowley | 264/277 |
| 4,496,352 | 1/1985 | Soika | 604/283 |
| 4,902,419 | 2/1990 | Shibata et al. | 428/36.9 |
| 5,176,637 | 1/1993 | Sagae | 604/283 |
| 5,312,377 | 5/1994 | Dalton | 604/283 |
| 5,405,668 | 4/1995 | Sandt | 428/35.7 |
| 5,601,894 | 2/1997 | Maruschak | 428/35.7 |
| 5,803,895 | 9/1998 | Kronholz et al. | 600/3 |

Primary Examiner—Jan H. Silbaugh
Assistant Examiner—Edmund H. Lee
Attorney, Agent, or Firm—Oblon, Spivak, McClelland, Maier & Neustadt, P.C.

[57] ABSTRACT

A process for producing a flexible plastic molding with one or more catheters or tubes embedded equidistantly therein which comprises firmly clamping the catheters or tubes in a liquid or semi-gelled paste comprising a precursor of the plastic material of the molding, in a gelling or hardening mold, and then carrying out complete gelling or hardening, and a product made by the process.

11 Claims, 4 Drawing Sheets

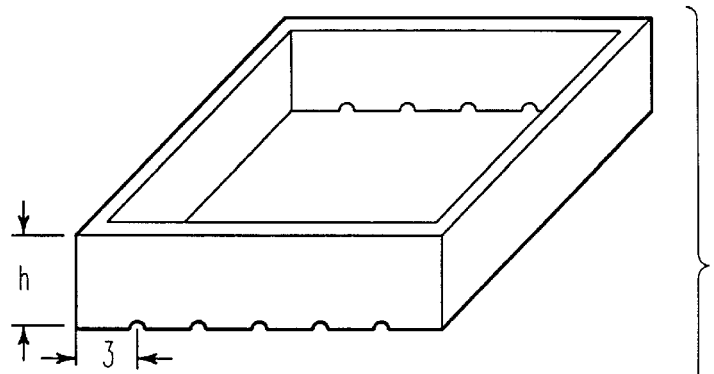
*FIG. 1A*
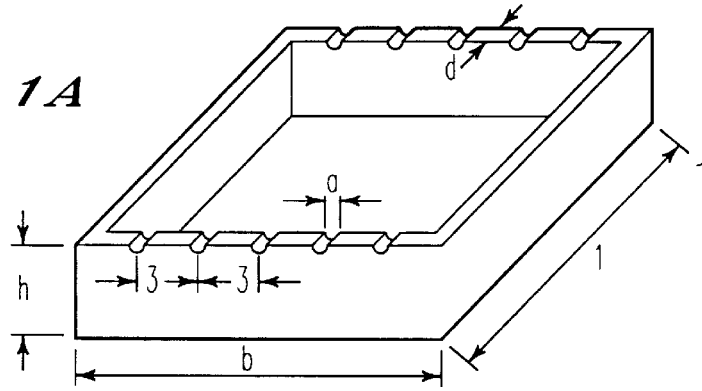
*FIG. 1B*
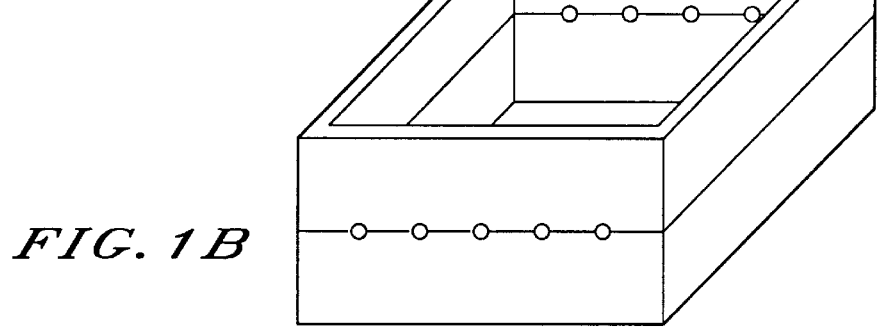
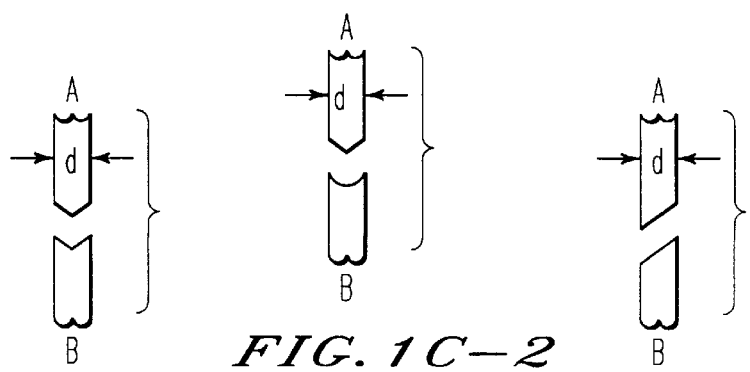
*FIG. 1C-1*   *FIG. 1C-2*   *FIG. 1C-3*

PROCESS FOR PRODUCING A FLEXIBLE PLASTIC GEL MOLDING WITH A PLURALITY OF CATHETERS EMBEDDED EQUIDISTANTLY THEREIN

BACKGROUND OF THE INVENTION

1. Field of the Invention

The present invention relates to flexible fixing materials for catheters and the like.

2. Discussion of the Background

For radiotherapy of tumors in body cavities, for example in the pharynx, intestine or vaginal regions and in body regions opened up by surgery, brachytherapy with catheters is a recognized method in which the radiation source or sources, controlled by an afterloading instrument, can be applied precisely to the treatment site in the body and can be moved such that a previously calculated course of the radiation dose over the treatment area results, as described by D. E. Wazer, R. Schmidt-Ullrich, W. Chasin, A. Wu, M. Buscher in Am. J. Otolaryngology 10 (3), (1989), 173, and by R. Stepan, P. Lukas, U. Fink, P. Knetschaurek, Ir. Siewert, M. Molls in "Intraoperative Radiotherapy with High Dose Afterloading (Flabs Method) in Colorectal Carcinom" (in F. W. Schildberg, N. Willich, H. -J. Krämling, "Intraoperative Radiation Therapy", Proceedings 4th International Symposium IORT, Munich 1992, Verlag Blaue Eule, Essen).

To avoid damage to patients and to ensure an exact irradiation plan, the catheters must be positioned accurately and fixed on or in the body. Only if this is ensured can the required course of isodoses be programmed and the planned irradiation be effected with the necessary safety and precision.

The usual practice for the production of fixed catheter sets is to cut rubber-like standard flat blocks (1 to 3 cm high, area: 30×30 cm; sources of supply are, for example, Quandt Medizintechnik, Hamburg, or Mick Radio Nuclear Instruments Inc. Bronx, N.Y.) to size and then to hollow a needle through them manually so that they can then be fitted with the catheters. This process has the disadvantage that because of the friction and adhesion between the outer wall of the needle and the flexible material, the rubber-like plastic body deforms and the parallel nature of the channels is lost.

Furthermore, these so-called flabs cannot be fixed reliably to the application site. Tears at the puncture site of the fixing thread and thus movement or even complete detachment of the flabs often occur.

Against this background, the invention of a flab fitted with catheters, in accordance with U.S. Pat. No. 4,963,128, was an advance, but this does not yet fully meet practical requirements.

Kneschaurek, Wehrmann, Hugo, Stepan Lukas and Molls in Strahlentherapie und onkologie 171 (1995), page 61, describe a cast silicone applicator which uses hollow plastic needles which are pushed parallel to one another into the central plane of the flab with the aid of a special device. However, the authors report difficulties in introduction of the needles, so that the cast silicone bodies must often be discarded.

Cylindrical plastic catheter systems likewise are not available. Plastic components bored through by the individual himself are therefore used as improvisation, as described in the publication cited above by D. E. Wazer et al., page 177.

SUMMARY OF THE INVENTION

The object of this invention was therefore to provide a process for the production of flexible moldings for fixing catheters or tubes which yields applicators which have catheters which run correctly parallel and are suitable for radiotherapy, in particular brachytherapy.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A and 1B shows two halves of a casting or gelling mold in open and closed configuration, respectively. FIGS. 1C-1, 1C-2 and 1C-3 show various embodiments for the shape of the sealing surfaces for holding catheters or tubes.

FIG. 2 shows a catheter with an adaptor on one end.

FIGS. 3A-1 and 3A-2 show a cylindrical mold with only an upper central piece equipped with a casting hole. FIGS. 3B-1 and 3B-2 show a prefabricated cylindrical fabric component.

DESCRIPTION OF THE PREFERRED EMBODIMENTS

This object is achieved according to the invention by a process for producing a flexible plastic molding with one or more catheters or tubes embedded equidistantly therein which comprises firmly clamping the catheters or tubes in a liquid or semi-gelled paste comprising a precursor of the plastic material of the molding, in a gelling or hardening mold, and then carrying out complete gelling or hardening. Requirements here are that the plastic surrounding the catheter should be soft and flexible and that the plastic material should have a density of 0.9 to 1.2 $g/cm^3$ and, given the duration of the application and severity of the indication, should not be injurious to health, and should be sterilizable by customary processes. Another characterizing feature of the present invention is the provision of this plastic/catheter system with a non-fibrous, body-friendly fabric of synthetic fiber incorporated under the surface over the entire area, or with a coaxial fabric of synthetic fiber on the lower part of the cylindrical body, in all cases on the side facing away from the irradiation side or away from the irradiation region. The catheter/plastic system according to the invention can thus be cut as desired, and they can be fixed reliably and without tearing in any desired manner and at any place.

Plastic materials which can be employed for guiding and fixing afterloading catheters are body-friendly, flexible plastics based on polyurethanes, polyolefins, polycarbonates, polyvinyl chloride, polysulfones, polyethers, polyesters, polyamides, polyacrylates, silicone rubbers, and analogous polymers with and without plasticizers, the densities of which are in the range from 0.8 to 1.5 $g/cm^3$ and which have the lowest possible absorption of γ-rays, are at least translucent and preferably transparent and can be sterilized by customary processes without the formation of harmful decomposition products. Gel-like polymer systems are in principle also suitable.

To produce the flat, square or rectangular applicators according to the invention, the catheters or tubes are drawn through the particular opposite bores of the casting or gelling molds, which can be made of glass, metal which cannot be attacked chemically or which has been coated on the surface—such as, for example, coated with polished gold rolled sheets—enamelled metals or glazed ceramics or also high-quality graphite, and are tensioned. It is essential when choosing a material for the casting or gelling mold that the material is dimensionally stable at the processing temperatures and neither undergoes chemical reactions with the casting and gelling medium which lead to caking or tissue-damaging, toxic or carcinogenic substances, nor releases substances which are likewise harmful from its inside to the plastic/catheter system. The casting and gelling molds furthermore must be easy to clean. It would also be advantageous if they could be sterilized for special requirements.

Figure 1D:
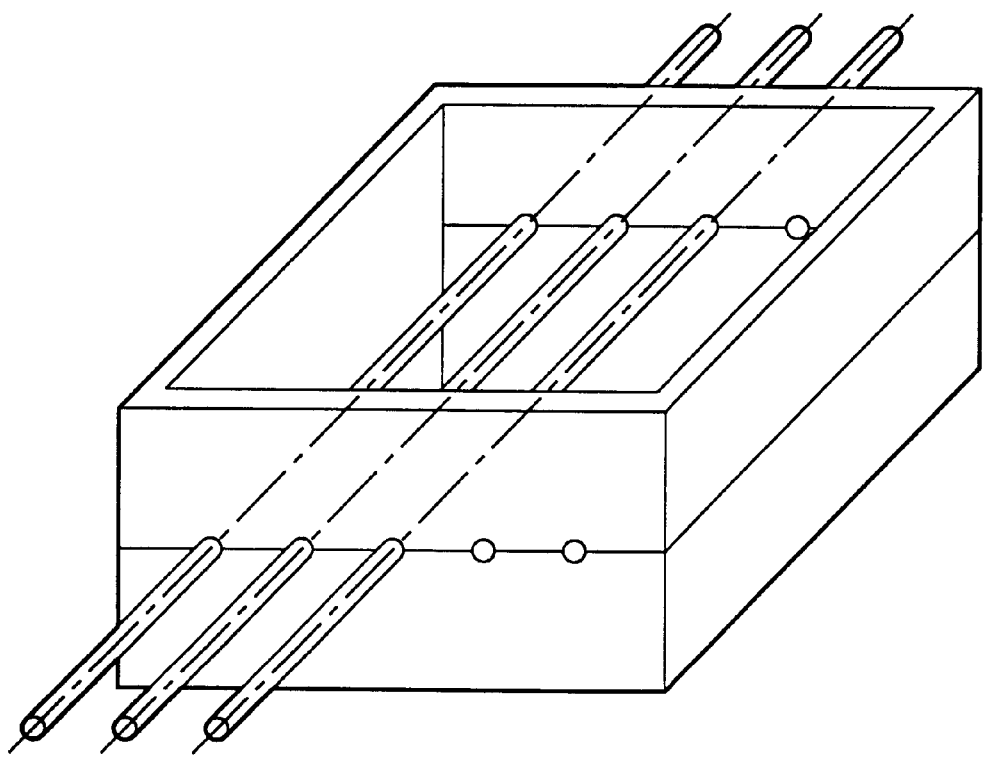
FIG. 1D shows the mold with the catheters inserted.
Figure 2:
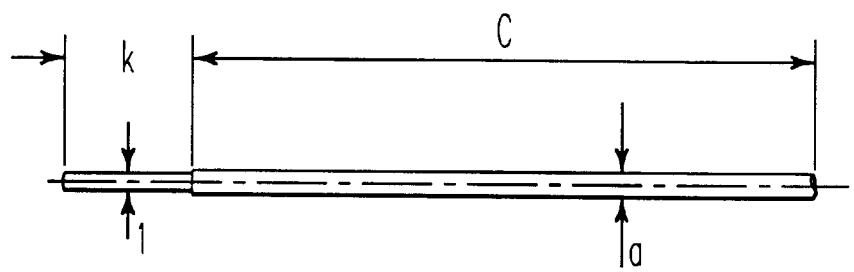
Figures 1, 3A:
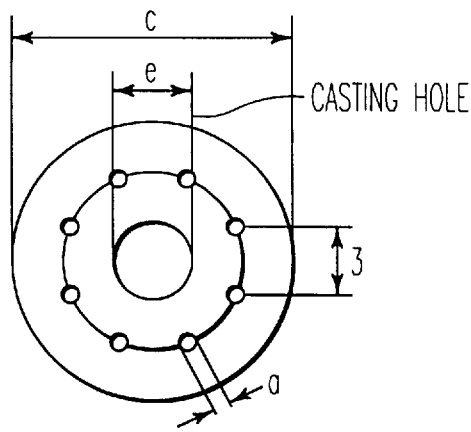
Figures 2, 3A:
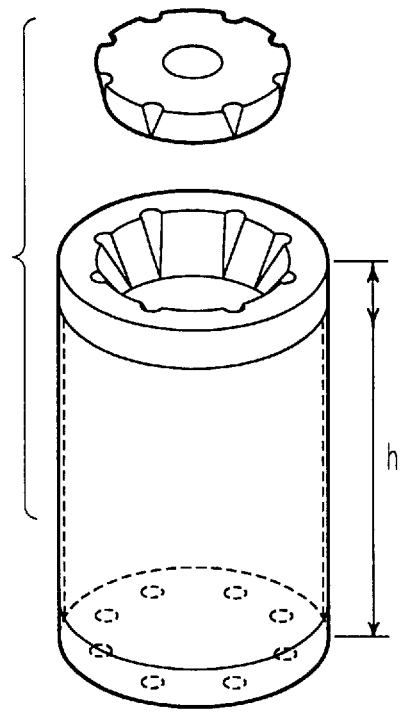
Figures 1, 3B:
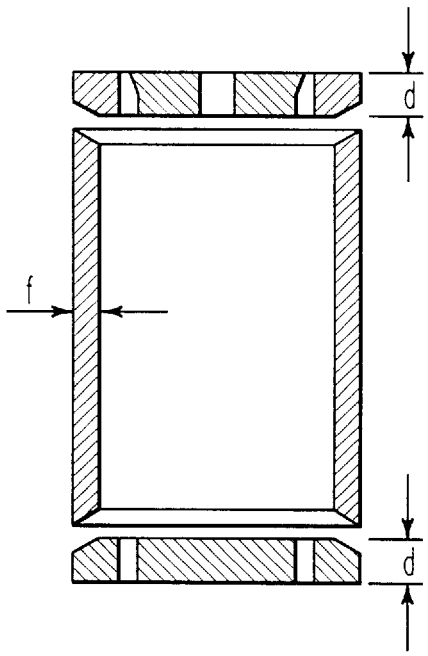
Figures 2, 3B:
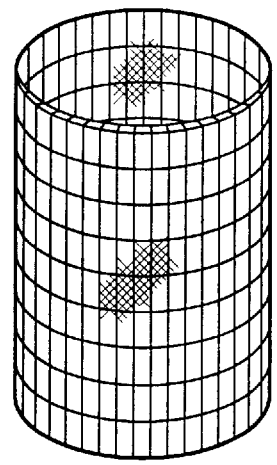

The sealing surfaces of the casting or gelling mold sections (FIGS. 1A, 1C-1 through 1C-3) are preferably to be angled, circular or conical in shape, in order to achieve a secure assembly and high tightness. In FIGS. 1A and 1C-1 throuth 1C-3, h stands for height of the casting mold, m stands for distance between the centers of two holes, a stands for external diameter of the catheter, b stands for total length of the casting mold, l stands for total width of the casting mold, and d stands for wall thickness of the casting mold.

After clamping of the catheters and assembly and if appropriate clamping together of the mold, the air-hardening or initiator-hardening or gelling liquid plastic material is poured into the mold until the liquid stands at a certain height above the clamped catheters. After brief initial hardening or gelling, the plastic fabric is inserted and the remaining amount of liquid starting material is introduced up to the required height. This is followed by final complete hardening or gelling of the plastic material. Complete gelling of the paste is effected according to the polymer used.

In the case of large bores for the catheters, adequate tightness with respect to the casting or gelling liquid can be achieved by filling with partly hardened or initially gelled material.

If the liquid casting or gelling material has to be processed at higher temperatures which are unacceptable for the clamped catheters, metal pins which are coated on the surface in the manner described above, corresponding to the diameter of the catheters, are provided with an adapter at one end (FIG. 2) so that the corresponding plastic catheter can be coupled without changing the outer diameter. After complete hardening or gelling of the plastic composition, the catheters can thus be drawn through the plastic body with the aid of the metal pins. Such an operation is preferably carried out still in the state of incomplete hardening or gelling and in the casting or gelling mold, so that the hardening or gelling plastic material presses close against the outer surfaces of the catheters. In FIG. 2, a stands for diameter of the metal rod; corresponds to the external diameter of the catheter, c stands for length of the metal rod within the casting mold, i stands for diameter of the metal pin outside the casting mold, corresponds to the internal diameter of the catheter, and k stands for length of the metal rod outside the casting mold.

To remove the finished applicator from cylindrical casting and gelling molds without problems after complete hardening, the cylindrical mold must comprise two halves, which can also be joined together tightly (FIGS. 3A-1 and 3A-2). The top and base are each composed of two ring halves and central pieces, only the upper central piece being equipped with a casting hole. All the components are preferably equipped with conical sealing surfaces which meet the sterility requirements by being ground to fit and, in the case of metals, by surface coatings. In FIGS. 3A-1 and 3A-2, a stands for external diameter of the catheter, c stands for external diameter of the round casting mold, d stands for wall thickness of the upper and lower lid, e stands for external diameter of the casting hole, f stands for wall thickness of the round casting mold, h stands for height of the round casting mold, and m stands for distance between the centers of two holes.

The cylindrical molds are either in an appropriate oven or are held together by a clamping device which is equipped with metal spiral springs in order to adapt to the thermal expansion.

The fabric component is prefabricated as a cylinder with dimensions according to requirements (FIGS. 3B-1 and 3B-2) and is inserted into the mold with the catheters or pins coated on the surface, before casting.

Figure 4A:
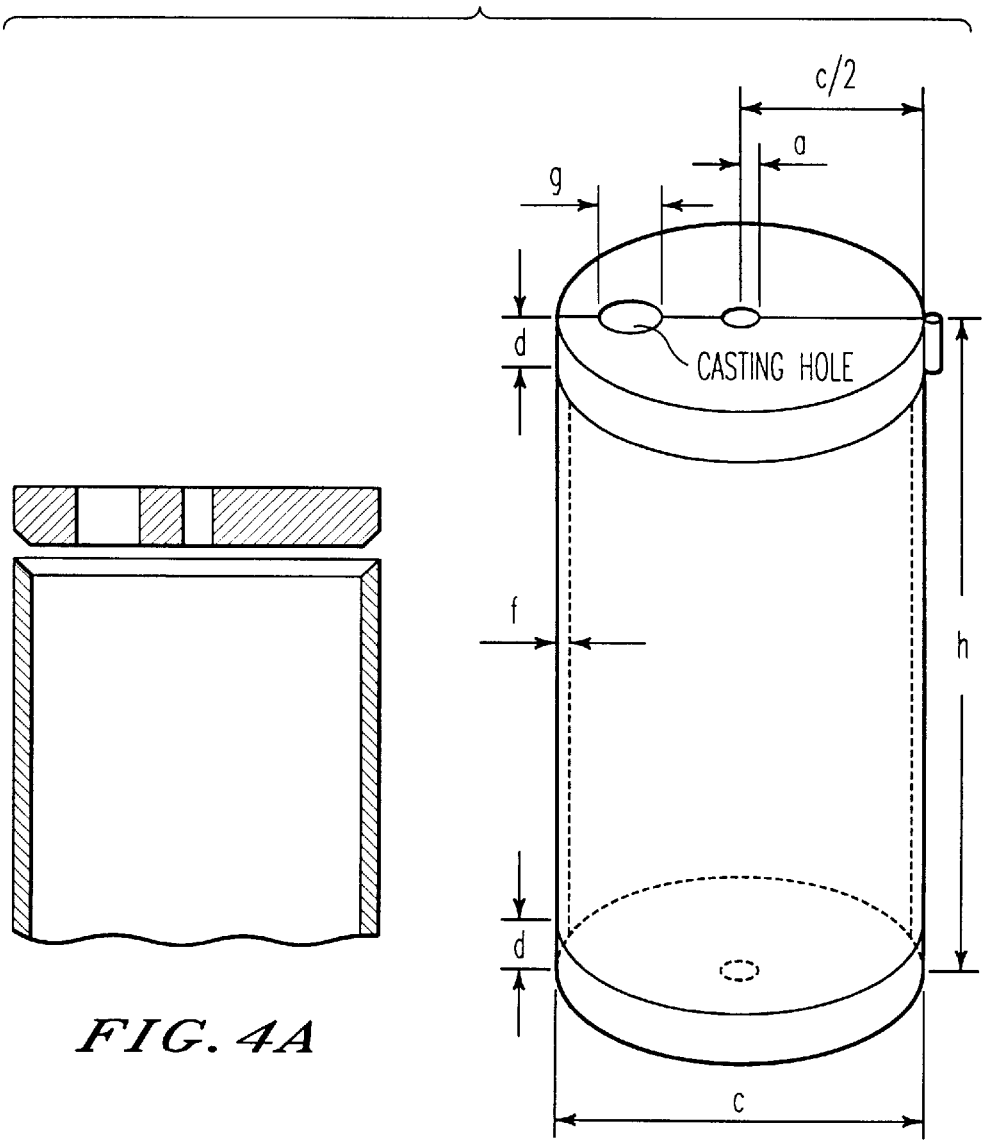
FIG. 4A shows a cylindrical mold designed for only one catheter.
Figure 4B:
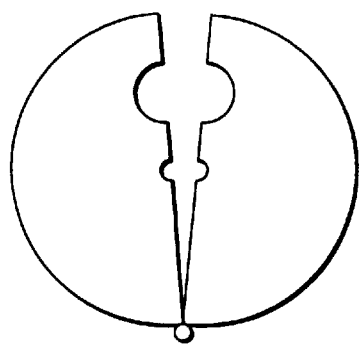
FIG. 4B shows one of the covers in two parts.

Narrow cylindrical molds which are to be fitted with only one individual catheter allow the finished applicator to be pulled out and are thus simpler to construct (FIG. 4A). Only one of the covers comprises two parts (FIG. 4B). In FIG. 4A, a stands for external diameter of the catheter, c stands for external diameter of the round casting mold, d stands for wall thickness of the upper and lower lid, f stands for wall thickness of the round casting mold, g stands for external diameter of the casting hole, and h stands for height of the round casting mold.

The dimensions of the figures are given only by way of example and are not limited to these. Plastic/catheter systems can be produced in any desired size by the processes according to the invention.

Having generally described this invention, a further understanding can be obtained by reference to certain specific examples which are provided herein for purposes of illustration only and are not intended to be limiting unless otherwise specified.

EXAMPLES

Free-flowing pastes of, for example, individual or several polyvinyl chloride polymers or polyacrylates, which can be made into pastes, with plasticizers or plasticizer mixtures are obtained by homogenization in dissolver or planetary mixers. Homo-, co- or terpolymers can be employed.

To regulate the viscosity and to provide thixotropic properties, colloidal silicic acids, metal soaps, glycerol mono-oleate and/or aluminum silicates or also magnesium silicates can be used. This is necessary in particular in order to stabilize the dispersions at plasticizer contents above 50%. Thixotropic agents are mixed into the pastes in amounts of 0.01 to 5 parts per 100 parts of polyvinyl chloride or polyacrylate.

The densities of the plastic/catheter systems can be adjusted by varying the plasticizers/polymer ratios.

Preparation of a Polyvinyl Chloride Gel

After 10 to 50% of the plasticizer (for example Edenol, di(ethylhexyl) phthalate) or the plasticizer mixture has been initially introduced, the entire polyvinyl chloride which can be made into a paste is admixed in a planetary mixer up to a temperature of 30° C. The remaining plasticizer contents are then added in portions. A total of 2 parts of glycerol monooleate are incorporated in portions into this composition as a thixotropic agent.

The resulting gelling composition is introduced into the gelling mold of glass, which in this case is provided with the metal pins described above instead of the catheters, such that the liquid composition stands 3 mm above the inserted pins. After initial gelling at 180° C. for 3 minutes, the heating unit is removed and, after cooling, the plastic fabric is inserted.

The remaining liquid composition is then added and gelling is carried out at 180° C. for 15 minutes.

After cooling to 120° C., the catheters, which are on the metal pins outside the gelling oven, can easily be pushed through the gelled plastic without damage to the catheters, the metal pins serving as a reliable, dimensionally correct guide for the catheters.

After cooling, the parts of the gelling mold can easily be removed without the gelled plastic composition sticking. Practically no shrinkage of the plastic/catheter body is detectable.

After removal of the plastic/catheter system, the outer surface is powdered with maize starch, whereupon a flexible, tissue-friendly and non-sticking surface is obtained. The density of the catheter produced in this manner is 1.15 g/cm$_3$. This applicator can then be cut to the geometric area required.

Production of a Flexible Polyacrylate Applicator

Mixing is initially carried out in the same manner as in the example for polyvinyl chloride, with the difference that 1% of hardener (for example hydrogen peroxide or potassium peroxodisulfate) is added. Complete hardening is carried out at 120° C. Under these conditions, the coated metal pins are not required, so that the catheters can be inserted before the casting and gelling operation.

The disclosure of German patent application 195 26 690.0, filed Jul. 21, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A process for producing a flexible plastic gel molding with a plurality of catheters embedded equidistantly therein, which comprises firmly clamping the catheters in a liquid or semi-gelled paste comprising a precursor of the plastic material of the molding, in a gelling mold, and then carrying out complete gelling of the liquid or semi-gelled paste thereby forming the flexible plastic gel molding with the plurality of catheters embedded equidistantly therein, wherein the plastic material includes a polymer selected from the group consisting of polyurethane, polyolefin, polycarbonate, polyvinyl chloride, polysulfone, polyacrylate, polyether, polyamide, and silicone polymers with or without a plasticizer.

2. The process as claimed in claim 1, wherein the catheters and a tissue-compatible fabric are introduced into the gelling mold prior gelling or to complete gelling.

3. The process as claimed in claim 1, wherein sealing surfaces of the mold are conical in shape.

4. The process as claimed in claim 1, wherein the mold comprises two half sections.

5. The process as claimed in claim 1, wherein the mold is cylindrical in shape.

6. The process as claimed in claim 1, wherein the polymer is polyvinyl chloride.

7. The process as claimed in claim 1, wherein the polymer is polyacrylate.

8. The flexible plastic gel molding with the plurality of catheters embedded equidistantly therein made by the process of claim 1.

9. The flexible plastic gel molding with the plurality of catheters embedded equidistantly therein made by the process of claim 2.

10. The flexible plastic gel molding with the plurality of catheters embedded equidistantly therein made by the process of claim 6.

11. The flexible plastic gel molding with the plurality of catheters embedded equidistantly therein made by the process of claim 7.

* * * * *